United States Patent [19]

Wells

[11] Patent Number: 5,332,512
[45] Date of Patent: Jul. 26, 1994

[54] ISOKINETIC DILUTER FOR PARTICLE MEASURING INSTRUMENT

[75] Inventor: David Wells, Arlington, Va.

[73] Assignee: Pacific Scientific Company, Newport Beach, Calif.

[21] Appl. No.: 43,147

[22] Filed: Mar. 31, 1993

Related U.S. Application Data

[63] Continuation of Ser. No. 810,134, Dec. 19, 1991, abandoned.

[51] Int. Cl.$^5$ .................... B01D 37/00; G01N 1/18
[52] U.S. Cl. .................... 210/790; 55/270; 73/28.01; 73/61.71; 73/863.23; 95/273; 210/434
[58] Field of Search ............ 210/433.1, 790, 96.1, 210/434, 243, 808; 55/97, 270, 309, 360; 73/28.01, 28.04, 28.05, 863.23, 61.71, 863.51, 61.41, 61.42, 61.72; 95/273

[56] References Cited

U.S. PATENT DOCUMENTS

| | | | |
|---|---|---|---|
| 1,100,171 | 6/1914 | Brown | 73/28.01 |
| 3,794,909 | 2/1974 | Smith | 55/270 |
| 3,841,145 | 10/1974 | Boubel | 73/28.04 |
| 3,853,750 | 12/1974 | Volsy | 55/270 |
| 3,890,122 | 6/1975 | Frantz | 55/212 |
| 3,892,549 | 7/1975 | Lyshkow | 55/270 |
| 3,954,428 | 4/1976 | Marple et al. | 55/270 |
| 3,986,386 | 10/1976 | Beltzer et al. | 73/28.04 |
| 4,372,859 | 2/1983 | Sugimoto et al. | 210/790 |
| 4,543,191 | 9/1985 | Stewart et al. | 73/61.41 |
| 5,109,708 | 5/1992 | Lawless | 73/28.01 |

FOREIGN PATENT DOCUMENTS

| | | | |
|---|---|---|---|
| 733853 | 4/1943 | Fed. Rep. of Germany | 55/270 |
| 3302906 | 12/1988 | Japan | 210/243 |
| 1183617 | 3/1970 | United Kingdom | 55/270 |

OTHER PUBLICATIONS

EPA Catalog No. EP75 "Emission Parameter Analyzer", Property of Joy Manufacturing Co. Western Precipitation Division, Printed Jun. 1972.

Primary Examiner—Joseph W. Drodge
Attorney, Agent, or Firm—Lane, Aitken & McCann

[57] ABSTRACT

A particle measuring and counting system employs an isokinetic diluter comprising a gas filter having a capillary tube extending through the middle of the filter. The capillary tube and filter are arranged to divide a stream entering the filter into an outer substream from which entrained particles are filtered and an inner substream containing a sample of the outer substream. The two substreams are mixed downstream of the capillary tube and the resulting diluted sample flows through the particle counting and measuring instrument.

20 Claims, 2 Drawing Sheets

ISOKINETIC DILUTER FOR PARTICLE MEASURING INSTRUMENT

This application is a file wrapper continuation of application Ser. No. 07/810,134, filed Dec. 19, 1991, now abandoned.

BACKGROUND OF THE INVENTION

Small particles entrained in a flowing stream of gas can be measured and counted by instruments which direct a beam of light through the stream of gas and detect the light scattered from individual particles entrained in the stream. The instruments provide a count of particles in each size range and thus measure the particle size distribution in the sample stream. Practical applications of these devices include use in measuring particle distribution in aerosols, monitoring of work place environments to ensure compliance with health and safety standards and the use in conjunction with clean room environments to insure that proper specifications are met in the manufacture of products which have rigid purity specifications.

Existing particle measuring instruments can accurately measure both the size and number of particles in a flowing stream under ideal conditions. However, when the concentration of particles entrained in a sample stream is great, the particle measuring instruments do not give accurate measurements of particle size distribution because individual particles cannot be discerned from the data generated by the photodetectors. The effective measurement limit of particle concentration for some commercially available particle measuring instruments is approximately to 1 million particles per cfm. For example, an instrument sold by the assignee of this invention and identified as the Hiac/Royco 5230 is estimated to be able to measure particles of various sizes up to concentrations of 1 million at 1 cfm.

In order to measure gas samples that have concentrations near and over 1 million particles per cfm and avoid the problems associated with this condition, the sample can be diluted with a known volume of gas or air having no particles. The actual concentration and composition of the unknown sample can then be calculated by applying ratio of dilution to the measurement of the diluted sample.

When diluting a sample it is important to ensure that the flow dynamics do not affect the particle size distribution in the diluted sample. In addition, the flow should be maintained in a turbulent state to keep the particles suspended in the gas. With improper flow dynamics, the ratio of large particles measured to small particles measured can become skewed and application of the ratio of dilution to the data will not accurately reflect the size concentrations of particles present in the undiluted stream. If the turbulence is not maintained in the system, larger particles entrained in the stream will settle out and the accuracy of the determination of the concentration of the larger particles will be reduced.

Attempts to dilute an air sample by using a collection device in the form of a small entrance port having a small opening, such as a needle valve and mixing the collected sample with filtered air has been unsatisfactory. The flow dynamics of the air entering a narrow opening affect the particle distribution because larger particles are excluded from or drop out of the sample stream passing through the restricted opening. Accordingly, the resultant data generated does not accurately reflect the particle size distribution suspended in the original gas sample.

SUMMARY OF THE INVENTION

The instant invention is a device and method which can accurately measure particles in high concentrations by accurately diluting a flowing sample stream of gas having particles entrained therein with a predetermined volume of gas devoid of particles. The device is able to dilute a flowing sample stream and maintain the ratios of particles in both size and number as they occur in an undiluted stream. The dilution device can be used with existing commercially available particle detectors and is intended to be placed in a stream of flowing gas or liquid upstream of a particle detection device. The dilution device is effectively isokinetic and maintains an even flow rate of gas throughout the system.

The diluter of the invention, consists of a capillary tube concentrically encircled by a second outer tube which has an entrance, a chamber, a filter element and an exit. The capillary tube is centrally positioned within the outer tube and extends from a position downstream from the entrance into the outer tube, through the filter element and out the chamber exit. The capillary tube divides a flowing stream of gas containing particles into two component sub-streams, an outer stream and an inner stream. The outer stream of air flows to the chamber and through a filter element which filters substantially all of the particles from the air stream. The filtered air, then essentially devoid of particles, passes through the chamber's exit port and into an exit tube where it mixes with the inner stream which flows through the capillary. The inner stream passes through an opening in an end wall of the filter element and remains unfiltered. Flow through the system is achieved by a pressure differential across the diluter provided by a suction pump.

The components of the device are chosen to keep the flow of the inner and outer streams isokinetic, which means that the average flow velocity of the outer stream is the same as that of the inner stream. The pressure of the air in the outer stream drops in pressure as it passes through the filter element. The capillary is designed so that this drop in pressure is equal to the pressure drop of the inner sub-stream as it passes through the capillary. Turbulence in the inner stream and in the exit tube where the streams mix is also maintained to keep the particles entrained in the gas in suspension. Turbulence is achieved in the capillary tube by selecting the size of the tube to be small enough relative to the flow rate.

In order to insure that the conditions of the system remain isokinetic, the length of the capillary must be carefully chosen in relation to the flow characteristics of the filter element. The device is able to dilute a sample by fixed ratio which is determined by the size of the capillary opening in relation to the diameter of the entrance port of the outer tube.

The invention is intended to be used in conjunction with a particle detection instrument capable of counting and measuring particles entrained in a flowing stream of air and ascertaining both the number and size of the particles.

DESCRIPTION OF A PREFERRED EMBODIMENT OF THE INVENTION

Figure 1:
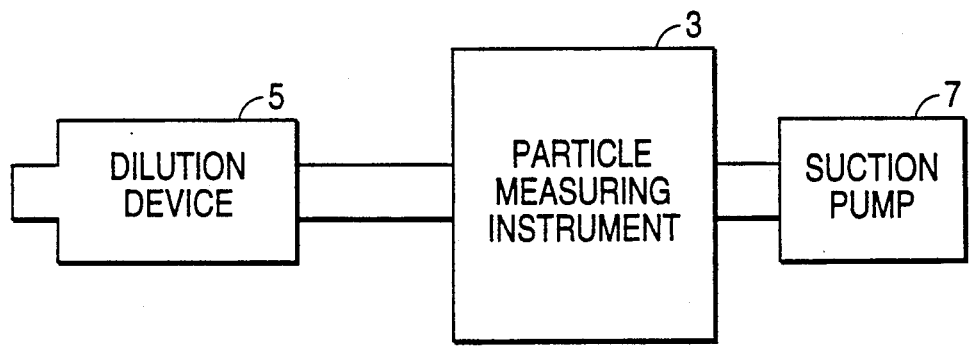
FIG. 1 is a schematic illustration of the particle measuring system of the invention.

As shown in FIG. 1, the particle measuring system of the invention comprises a particle measuring instrument 3 connected with a dilution device 5 and a suction pump 7. The suction pump draws sample air through the dilution device 5 into the particle instrument 3, which measures the size of the received particles and counts the numbers of particles in each size range. An example of the particle measuring instrument is disclosed in the VonBargen patent U.S. Pat. No. 4,842,406, issued Jun. 27, 1989. This patent is hereby incorporated by reference.

Figure 2:
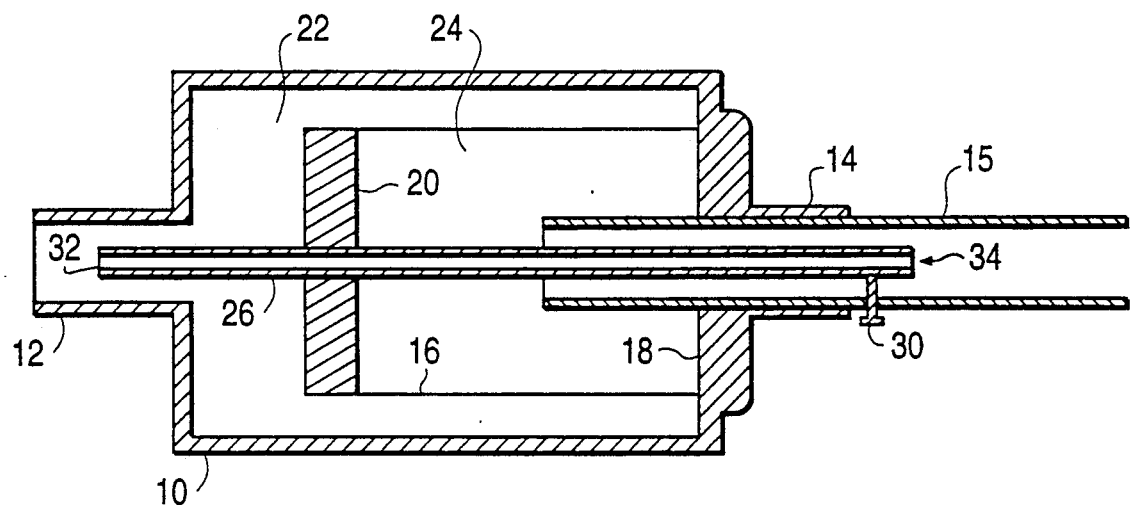
FIG. 2 is a cross section of the dilution device of the invention.
Figure 3:
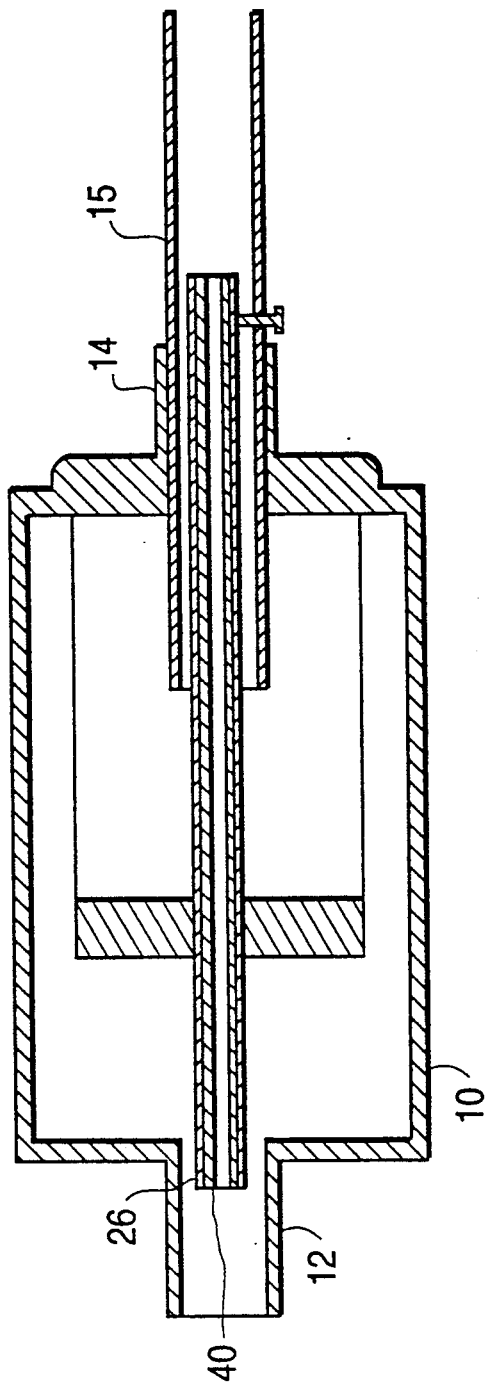
FIG. 3 is a cross section of the system of FIG. 2 modified to provide a greater dilution ration.

As shown in FIG. 2, the diluter according to the invention comprises a cylindrical housing 10 having a tubular entrance port 12 and a tubular exit port 14. Within the chamber defined by the housing 10 is a filter element 16 attached by an air tight seal to a circular rear wall 18 of the chamber. Filter element 16 is cylindrical in shape and is sealed on the opposite side by an impermeable end wall 20. The filter element is typically constructed of air permeable or porous pleated air filter paper as the filter medium which make up the sides of the filter and connects rear wall 18 to end wall 20. The end of the filter element 16 which is secured to the rear end wall 18 of chamber 10 is concentric with the exit port 14. The filter element 16 divides the chamber into two sub-chambers, a proximal sub-chamber 22 and a distal sub-chamber 24.

A capillary tube 26 having a circular cross section is concentrically positioned on an axis which runs through entrance port 12 and exit port 14. The capillary passes through a hole in circular end wall 20. Circular end wall 20 centrally supports the capillary within chamber 10. Capillary tube 26 provides a passage for unfiltered air between the two regions of the device separated by filter element 16. A brass extension tube 15 connects the exit port 14 to the particle measuring and counting instrument 3.

The capillary is preferably made of a metal or an electrically conductive material. However a glass or plastic capillary could be employed. A conductive material is preferred because particles having a small electric charge could apply a charge to the capillary and effect the flow of particles through the system. To prevent the build up of an electric charge on the capillary, a grounding element 30 connects the capillary to an external ground which dissipates any electrical charge.

As shown in FIG. 1 the grounding element 30 is a pin that extends radially from the walls of the extension tube 15 and grasps the outside of the distal end of capillary 26 within the extension tube 15. The pin stabilizes capillary 26 and dissipates electric charge to the extension tube 15. The extension tube 15 fits within the exit port 14 and extends from about the middle of the sub-chamber 24. The extension tube 15 physically supports the diluter and provides an electrically conductive path to the particle detector 3 which is grounded.

In operation, air or gas containing particles flows through the entrance port 12 in the direction of arrow A. The particle sizes may range from 0.1 microns to 100 microns in diameter. The dilution system will also work on particles outside of this range provided the filters and the particle measuring instrument are effective at these extremes. The flow of gas is maintained turbulent throughout the system to keep particles suspended in the gas. In entrance port 12 the stream of gas encounters capillary tube 26 which divides the flow into two sub-streams, an inner stream and an outer stream. In order to keep the flow turbulent, the Reynolds number of the system, which reflects a system's relative turbulence, should have a value of over 4,000. The Reynolds number, "Re", is a function of the inertia force divided by the viscous force of a system. Large Reynolds' numbers indicate large inertial forces compared to viscous forces and the condition indicates a turbulent flow while small Reynolds' numbers are associated with laminar flow. The Reynolds number for air flowing through a cylindrical tube at standard temperature and pressure is determined by the following simplified equation.

$$Re = 1600 \times (\textit{flow in cfm})/(\textit{diameter in inches})$$

The 10 to 1 (10x) diluter of a specific embodiment of the invention operated at 1 cfm would have a flow rate of 0.1 cfm in the capillary tube. To maintain turbulence in the capillary, the above formula indicates that the inner diameter should be less than 0.04 inches to maintain turbulence. In the 10x diluter, the inner diameter is 1/16 (0.063) inches.

It is important to maintain the flow turbulent within the capillary tube 26 and in the exit tube 15 downstream from the capillary tube 34 where the inner substream mixes with the outer substream.

Flow of inner stream through capillary 26 is resisted by friction between the stream and the inner wall of the capillary tube. Flow in the outer stream is restituted by the filter element 16 in the housing 10. The flow resistance results in a pressure drop from capillary entrance 32 to capillary exit 34 and from one side of the filter element to the other. These pressure drops should be approximately the same.

The diameter of capillary entrance 32 must have proper dimensions to meet the condition of keeping the system isokinetic meaning that the flow velocity at the entrance to the capillary tube is the same as the average flow velocity of the stream flowing towards the filter at the point where the streams diverge. The size of the entrance port 32 which achieves this result surprisingly does not require the entrance port to be flared. An initial embodiment was constructed (not shown) that employed a capillary with a flared opening. In a theoretical model having uniform air flow, one would expect that the ratio of the area of the opening of the capillary compared to the area of the entrance port would also be the ratio of dilution. A first embodiment of a dilution device intended to dilute a sample by ten fold was constructed using a capillary having a cross section of approximately 1/50 of the cross section of the entrance port of the diluter. One opening of the capillary was flared open to approximately 1/10th of the area of the entrance port of the diluter. Empirical test results of this device showed the flared design to be non-isokinetic and the data generated tended to skew data towards overestimating the concentration of large particles and not diluting the sample to the expected degree. By incrementally decreasing the size of the opening by shortening the length of the inlet flare, proper isokinetic data was eventually obtained. These experiments unexpectedly showed the best design used a capillary without a flared opening but instead a capillary with an entrance the same size as the size of the remainder of the capillary tube. This result is obtained because the reduced volume of flow through the capillary resulting from the disturbance to the flow caused by the capillary walls at the entrance 32 is apparently offset by the velocity profile in the flow existing across the gas stream in the entrance port 12.

The outer stream of gas flows to chamber 10 where the filter element 16 is located. Preferably the filter element is cylindrical. However, any shape filter with the correct surface area and permeability factors would satisfactory achieve the objectives of the invention. The outer air stream flows through filter element 16 and particles entrained in the gas are trapped in the filter medium. The effect of the filter on the flow of gas does not appreciably change with time or the volume of particles trapped in the filter as might be expected. As the gas passes through the filter element 16 there is a pressure drop from the proximal sub-chamber 22 to the distal sub-chamber 24. This pressure drop remains fairly constant over the life of the filter and the invention takes advantage of this characteristic. Because the flow dynamics of the air passing trough the filter remain fairly constant over time, a constant volume of clean air, or air containing no particles, exits the distal sub-chamber 24 of filter chamber 10. Clean air exiting the chamber is mixed with the inner stream of air containing particles in extension tube 15 of the diluter.

In order to maintain an even volumetric flow of air while preserving the turbulence required to keep the particles suspended, the pressure drop through the filter is made to be substantially the same as the pressure drop in the stream flowing through the capillary tube 26. This is done by precisely selecting and matching the components of the system including the diameter and length of the capillary 26, chamber 10, exit port 14, and exit port 15, and the flow characteristics of the filter element 16.

After the two streams are merged, the diluted stream is directed through the extension tube 15 to the particle detector 34 as shown in FIG. 3.

Example 1

An isodiluter according to the invention was constructed using a copper capillary tube having 1/16" inner diameter capillary and a length of 4", and a Gelman 0.45 micron filter (No. 12123, No. 960-272-03). The Gelman 0.45 micron filter is rated for use in liquid and is effective in removing particles down to 0.05 microns in air. This prototype diluter was tested at a flow rate of 1 cfm through the system and the following data was obtained:

| Particle Size | No. of Particles Measured Undiluted Sample Per cfm | Number of Particles Measured in Diluted Sample Per cfm | Ratio |
|---|---|---|---|
| >0.3 | 1,738,341 | 778,977 | 2.23 |
| >0.5 | 230,858 | 21,767 | 10.6 |
| >1.0 | 19,623 | 2,097 | 9.35 |
| >2.0 | 3,469 | 390 | 8.89 |
| >5.0 | 189 | 19 | 9.95 |
| >10.0 | 23 | 1 | 23.0 |

The data reflects that the predicted dilution ratio of 10:1 was successfully achieved. The isodiluter was able to consistently dilutes a samples set to measure particle sizes between 0.5 microns and 2 microns at a ratio of approximately 9.6 to 1. The data reflects the fact that there was a high concentration of particles smaller than 0.5 microns and the measuring device was not able to detect particles at concentrations exceeding 1 million per cubic foot in the undiluted sample.

Example 2

In some instances concentrations of particles in ambient air are very high and a diluter is required that will dilute the sample to a greater degree. The diluter as described above was fitted with a second copper capillary tube 40 inserted within the 1/16" capillary tube 26 to increase the dilution ratio to 50 to 1 (50X) as shown in FIG. 3. The second inner capillary tube has an inner diameter of 0.020". In this embodiment the rate of flow through the inner capillary is decreased to approximately 0.02 cfm. To maintain turbulence in the capillary tube with a flow rate of 0.02 cfm, the diameter of the capillary should be smaller than 0.0335 inches which is achieved in the specific embodiment of the 50X diluter by using the capillary with the inner diameter of 0.020 inches. Use of the diluter with the smaller capillary resulted in the following data:

| Particle Size | Diluted 10 × Per cfm | Diluted 50 × Per cfm | Ratio of 50 × Dilution to 10 × Dilution |
|---|---|---|---|
| >0.3 | 778,967 | 180,325 | 4.31 |
| >0.5 | 21,767 | 3,727 | 5.84 |
| >1.0 | 2,097 | 365 | 5.74 |
| >2.0 | 3,469 | 81 | 4.81 |
| >5.0 | 19 | 6 | 3.16 |
| >10.0 | 1 | 1 | 1.0 |

The smaller capillary results in a diluter effective at diluting a sample concentration at a ratio of approximately 50 to 1.

Both specific embodiments of the diluter provide a dilution in which the distribution of particles in the diluted sample is accurately maintained thus enabling an accurate measurement of the particle distribution in the original sample.

The above-described dilution system and method is described with reference to measuring particles entrained in an air stream. With modification of the filter to be a liquid filter, the method is also applicable to particles entrained in liquid streams.

I claim:

1. An apparatus for the dilution of fluids entraining particles comprising:

a chamber having an entrance port and an exit port and defining a flow path arranged to pass fluid from said entrance port to said exit port, a permeable filter medium in said chamber separating said flow path into a proximal region and a distal region, said entrance port located in said proximal region and said exit port located in said distal region, said filter medium being arranged to trap particles entrained in fluid passing from said proximal region to said distal region through said filter medium.

a tube having a proximal end and a distal end, said tube connecting said proximal region to said distal region, said tube having a size and orientation so as to result in a flow volume of the fluid flowing into said entrance port having the same size distribution of entrained particles as that of a flow volume of fluid flowing out of said distal end of said tube.

2. An apparatus as recited in claim 1, wherein said tube is constructed to have a pressure drop through the tube equal to the pressure drop through said filter medium.

3. An apparatus as recited in claim 1, wherein the proximal end of said tube is radially centered in said entrance port.

4. An apparatus as recited in claim 3, wherein said entrance port defines a flow channel having an entrance and wherein said proximal end to said tube is spaced downstream from the entrance to said flow channel.

5. An apparatus as recited in claim 1, wherein said tube is electrically conductive and is grounded.

6. An apparatus as recited in claim 1, wherein said filter medium and said tube are constructed so that the average velocity of flow in a fluid stream flowing toward said filter medium around the proximal end of said tube is equal to the velocity of flow at the entrance to said tube.

7. A particle measuring system comprising an apparatus for dilution of fluids as recited in claim 1, an instrument for measuring the sizes of particles entrained in a stream and means to draw a sample gas stream through said apparatus for dilution and then through said instrument.

8. An apparatus as recited in claim 1, wherein said tube defines an unobstructed constant diameter channel throughout its length and has an entrance opening at its proximal end of substantially the same diameter as said channel.

9. A method of determining the size distribution of particles in a flowing fluid sample containing particles suspended therein, comprising dividing the flowing fluid sample into a first and second sub-stream, filtering the particles from said first sub-stream to form said first sub-stream into a filtered steam while leaving particles suspended in said second sub-stream in the same size distribution as in said fluid sample, and then mixing said filtered stream and said second sub-stream together into a combined stream and measuring the size distribution of the particles in said combined stream.

10. An apparatus for dilution of fluids entraining particles comprising: a chamber having an entrance port and an exit port and defining a flow path to pass fluid from said entrance port to said exit port, the entrance port defining a direction of flow in said entrance port for fluid passing through said chamber from said entrance port to said exit port, a permeable filter medium in said chamber separating said chamber into a proximal region and a distal region, said filter medium being arranged to trap particles from fluid passing from said proximal region to said distal region through said filter medium, said entrance port located in said proximal region and said exit port located in said distal region and a tube having a proximal end and a distal end, said tube connecting said proximal region to said distal region, said tube having an entrance opening in said proximal end facing the direction of flow in said entrance port and being constructed and arranged so that the fluid flowing into said entrance port is isokinetically divided into flows around the proximal end of said tube and into the entrance opening of said tube.

11. An apparatus as recited in claim 10, wherein said tube is constructed to have a pressure drop through the tube equal to the pressure drop through said filter medium.

12. An apparatus as recited in claim 10, wherein said tube is electrically conductive and is grounded.

13. An apparatus as recited in claim 10, wherein said filter medium and said tube are constructed so that the average velocity of flow in a fluid stream flowing toward said filter medium around the proximal end of said capillary tube is equal to the velocity of flow at the entrance to said tube.

14. An apparatus as recited in claim 10, wherein said tube defines an unobstructed constant diameter channel throughout its length and has an entrance opening at its proximal end of substantially the same diameter as said channel.

15. A particle measuring system comprising an apparatus for dilution of fluids, an instrument for measuring the sizes of particles entrained in a stream and means to draw a sample gas stream through said apparatus for dilution and then through said instrument, said apparatus comprising a chamber having an entrance port and an exit port and defining a flow path to pass fluid from said entrance port to said exit port, the entrance port defining a direction of flow in said entrance port for fluid passing through said chamber from said entrance port to said exit port, a permeable filter medium in said chamber separating said chamber into a proximal region and a distal region, said filter medium being arranged to trap particles from fluid passing from said proximal region to said distal region through said filter medium, said entrance port located in said proximal region and said exit port located in said distal region and a tube having a proximal end and a distal end, said tube connecting said proximal region to said distal region, said tube having an entrance opening in said proximal end facing the direction of flow in said entrance port and being constructed and arranged so that the fluid flowing into said entrance port is divided into flows around the proximal end of said tube and into the entrance opening of said tube.

16. A method of diluting a flowing fluid sample containing particles suspended therein, comprising dividing the flowing fluid sample into a first and second sub-stream, filtering the particles from said first sub-stream to form said first sub-stream into a filtered stream while leaving particles suspended in said second sub-stream in the same size distribution as in said fluid sample, and then mixing said filtered stream and said second sub-stream together, the pressure drop through the length of travel of said first stream during said filtering being substantially equal to the pressure drop through the length of said second sub-stream.

17. A method of diluting a flowing fluid sample containing particles suspended therein, comprising dividing the flowing fluid sample into a first and second sub-stream, filtering the particles from said first sub-stream to form said first sub-stream into a filtered stream while leaving particles suspended in said second sub-stream in the same size distribution as in said fluid sample, and then mixing said first filtered stream and said second sub-stream together, the flow in said second sub-stream being maintained turbulent throughout said second sub-stream.

18. A dilution method as recited in claim 17, wherein the flow where said first and second streams are mixed is maintained turbulent.

19. An apparatus for dilution of fluids entraining particles comprising: a chamber having an entrance port and an exit port and defining a flow path to pass fluid from said entrance port to said exit port, the entrance port defining a direction of flow in said entrance port for fluid passing through said chamber from said entrance port to said exit port, a permeable filter medium in said chamber separating said chamber into a proximal region and a distal region, said filter medium being arranged to trap particles from fluid passing from said proximal region to said distal region through said filter medium, said entrance port located in said proximal region and said exit port located in said distal region and a tube having a proximal end and a distal end, said tube connecting said proximal region to said distal region, said tube having an entrance opening in said proximal end radially centered in said entrance port and facing the direction of flow in said entrance port and being constructed and arranged so that the fluid flowing into said entrance port is divided into flows around the proximal end of said tube and into the entrance opening of said tube.

20. An apparatus as recited in claim 19, wherein said entrance opening of said tube is spaced downstream of the entrance to said entrance port.

* * * * *